United States Patent [19]
Yesudas et al.

[11] Patent Number: 5,635,631
[45] Date of Patent: Jun. 3, 1997

[54] DETERMINING FLUID PROPERTIES FROM PRESSURE, VOLUME AND TEMPERATURE MEASUREMENTS MADE BY ELECTRIC WIRELINE FORMATION TESTING TOOLS

[75] Inventors: Michael Yesudas; John M. Michaels; Saeed Rafie; Than Shwe, all of Houston, Tex.

[73] Assignee: Western Atlas International, Inc., Houston, Tex.

[21] Appl. No.: 490,944

[22] Filed: Jun. 15, 1995

Related U.S. Application Data

[63] Continuation-in-part of Ser. No. 48,814, Jun. 16, 1993, Pat. No. 5,473,939, which is a continuation-in-part of Ser. No. 903,088, Jun. 19, 1992, abandoned.

[51] Int. Cl.$^6$ ............................................. G01N 7/00
[52] U.S. Cl. ..................... 73/61.46; 73/61.47; 73/19.05; 73/152.18
[58] Field of Search .................. 73/61.46, 61.47, 73/152.18, 152.51, 19.05

[56] References Cited

U.S. PATENT DOCUMENTS

| | | | |
|---|---|---|---|
| 4,782,695 | 11/1988 | Glotin et al. | 73/152.18 X |
| 4,862,729 | 9/1989 | Toda et al. | 73/19.05 |
| 4,994,671 | 2/1991 | Safinya et al. | 250/255 |
| 5,329,811 | 7/1994 | Schultz et al. | 73/152.51 X |
| 5,377,755 | 1/1995 | Michaels et al. | 166/264 |
| 5,386,718 | 2/1995 | Proffitt et al. | 73/61.46 X |
| 5,415,024 | 5/1995 | Proffitt et al. | 73/61.46 X |

Primary Examiner—Hezron E. Williams
Assistant Examiner—Daniel S. Larkin
Attorney, Agent, or Firm—Richard A. Fagin

[57] ABSTRACT

A method of determining an amount of dissolved gas in a fluid sample is disclosed. The method includes hydraulically confining and expanding the sample while measuring pressure and volume. A first volume and pressure are determined at which the rate of change in pressure with respect to volume deviates from a linear relationship. A second volume and pressure at which continued expansion of the fluid causes substantially no change in pressure is determined. The first pressure and volume are extrapolated by the linear relationship to intersect an extrapolation from the second volume and pressure at no change in pressure, thereby determining a bubble point comprising a bubble point pressure and a bubble point volume. A third pressure corresponding to measured pressure of the fluid sample at the bubble point volume is determined. An extrapolated sample volume is determined at the third pressure by extrapolating the linear relationship from the bubble point to a sample volume along the linear relationship corresponding to the third pressure. A volume of gas dissolved in the fluid sample is determined by linearly scaling a difference between the bubble point volume and the extrapolated sample volume with respect to a difference between the second volume and the bubble point volume.

In a preferred embodiment of the invention, the sample is withdrawn into a sample chamber in an electric wireline formation test tool having a means for measuring pressure and volume of the sample chamber.

6 Claims, 6 Drawing Sheets

DETERMINING FLUID PROPERTIES FROM PRESSURE, VOLUME AND TEMPERATURE MEASUREMENTS MADE BY ELECTRIC WIRELINE FORMATION TESTING TOOLS

CROSS-REFERENCE TO RELATED APPLICATIONS

The present application is a continuation-in-part of U.S. patent application Ser. No. 08/048,814, filed on Jun. 16, 1993 and entitled "Method and Apparatus for Pressure, Volume and Temperature Measurement and Characterization of Subsurface Formations", now U.S. Pat. No. 5,473,939, which is itself a continuation-in-part of U.S. patent application Ser. No. 07/903,088, filed on Jun. 19, 1992, now abandoned.

BACKGROUND OF THE INVENTION

1. Field of the Invention

The present invention is related to the field of electric wireline tools used to withdraw samples of fluids from earth formations. More specifically, the present invention is related to methods of determining various properties of fluids in earth formations by interpreting pressure and temperature readings made by electric wireline formation testing tools.

2. Description of the Related Art

Electric wireline formation testing tools are used to withdraw samples and to make pressure and temperature measurements of fluids contained within pore spaces of earth formations. Calculations made from these measurements can be used to assist estimation of the total fluid content within the earth formations.

As known in the art, a formation testing tool is typically lowered at one end of an armored electrical cable into a wellbore drilled through the earth formations. The formation testing tool typically includes a housing from which a tubular probe is extended and impressed onto the wall of the wellbore. The probe typically is externally sealed by an elastomeric packing element to exclude fluids from within the wellbore itself from entering the interior of the probe while fluids are withdrawn from the earth formation through the probe. Various selective valves in the tool place the probe in hydraulic communication with sample chambers included in the tool. Hydraulic lines which connect the probe to the various sample chambers can also be connected to a highly accurate pressure sensor for measuring the fluid pressure within the hydraulic lines. Other sensors in the tool can make measurements related to the volume of fluid which has entered some of the sample chambers during a test of a particular earth formation. The formation testing tool can also include a sample tank which can be selectively hydraulically connected to the probe so that a quantity of fluid withdrawn from the formation can be dispensed into the sample tank and transported to the earth's surface for laboratory analysis.

It is important to the wellbore operator to be able to determine that the fluid actually dispensed into the sample tank consists primarily of native fluid from within the pore space of the earth formation. In certain circumstances fluids other than the native fluid can be dispensed into the sample tank. For example, when a wellbore is drilled through the earth formations, it is typically filled with a liquid suspension, called "drilling mud". Drilling mud usually has a specific gravity great enough to exert hydrostatic pressure against the earth formations which can restrain the native fluids in the formations from entering the wellbore. It is even more typical for the hydrostatic pressure of the drilling mud to at least slightly exceed the native fluid pressures in the formations. If the drilling mud has a higher hydrostatic pressure than the native fluid pressure, the liquid phase of the drilling mud, called "mud filtrate", can be forced into the pore space in the formation by differential pressure in a process known as "invasion". An indeterminate volume of mud filtrate will be withdrawn from the formation when the probe is first hydraulically connected to the sample chamber or sample tank. Further, the probe is typically substantially filled with drilling mud when it is first hydraulically connected to the sample chamber.

If sufficient mud filtrate volume invades the earth formation, it may be necessary for the test tool operator to withdraw a very large volume of fluid from the earth formation before native fluid can be extracted therefrom and dispensed into the sample tank. It is of interest to the test tool operator to be able to determine when the fluid being withdrawn from the formation comprises native fluid so that the amount of time during which the formation test tool is locked in place can be kept to a minimum for reasons of safety as is understood by those skilled in the art.

It is known in the art to determine whether the fluid being withdrawn from the earth formation comprises native fluid by making certain measurements of the fluid as it is withdrawn through the probe. For example, U.S. Pat. No. 4,994,671 issued to Safinya et al, discloses the use of a near infrared spectrograph to determine the composition of fluid being withdrawn through the probe.

A drawback to the system disclosed in the Safinya et al '671 patent for determining the composition of fluid being withdrawn through the probe is that the spectrograph is sensitive to changes in transparency of a sample chamber window through which light must pass in order to make the spectrographic measurements of the fluid under test. Deposition of opaque materials on the window can reduce its transparency so as to make the spectrograph inoperative. Opaque materials can include certain high molecular weight hydrocarbons which may be present in some native fluids, or solid materials such as sand grains or clay particles which may break away and flow from the earth formation under certain conditions.

A further drawback to the system disclosed in the Safinya et al '671 patent is that gas bubbles, which may be present in some fluid samples, can disrupt the operation of the spectrograph, making it difficult to determine whether native fluid is being withdrawn into the probe. Gas can be present in some samples as a result of exsolution of dissolved gas as the sample pressure is reduced to enable flow into the sample chamber. Dissolved gas can be present in native crude oil in the earth formation.

It is an object of the present invention to provide a method of determining the properties of fluid withdrawn through the probe of a formation testing tool which does not require the use of a spectrographic sensor.

It is a further object of the present invention to provide a method of determining properties of fluid withdrawn through the probe of a formation testing tool which is functional in the presence of gas in a sample of the fluid.

SUMMARY OF THE INVENTION

The present invention is a method of determining an amount of dissolved gas in a fluid sample. The method includes hydraulically confining and expanding the sample while measuring pressure and volume of the sample. A first volume and pressure are determined at which the rate of change in pressure with respect to volume deviates from a linear relationship. A second volume and pressure at which continued expansion of the fluid causes substantially no change in pressure is determined. The first pressure and volume are extrapolated by the linear relationship to intersect an extrapolation from the second volume and pressure at no change in pressure, thereby determining a bubble point comprising a bubble point pressure and a bubble point volume. A third pressure corresponding to measured pressure of the fluid sample at the bubble point volume is determined. An extrapolated sample volume is determined at the third pressure by extrapolating the linear relationship from the bubble point to a sample volume along the linear relationship corresponding to the third pressure. A volume of gas dissolved in the fluid sample is determined by linearly scaling a difference between the bubble point volume and the extrapolated sample volume with respect to a difference between the second volume and the bubble point volume.

In a preferred embodiment of the invention, the sample is withdrawn into a sample chamber in an electric wireline formation test tool having a means for measuring pressure and volume of the sample chamber.

DESCRIPTION OF THE PREFERRED EMBODIMENT

Figure 1:
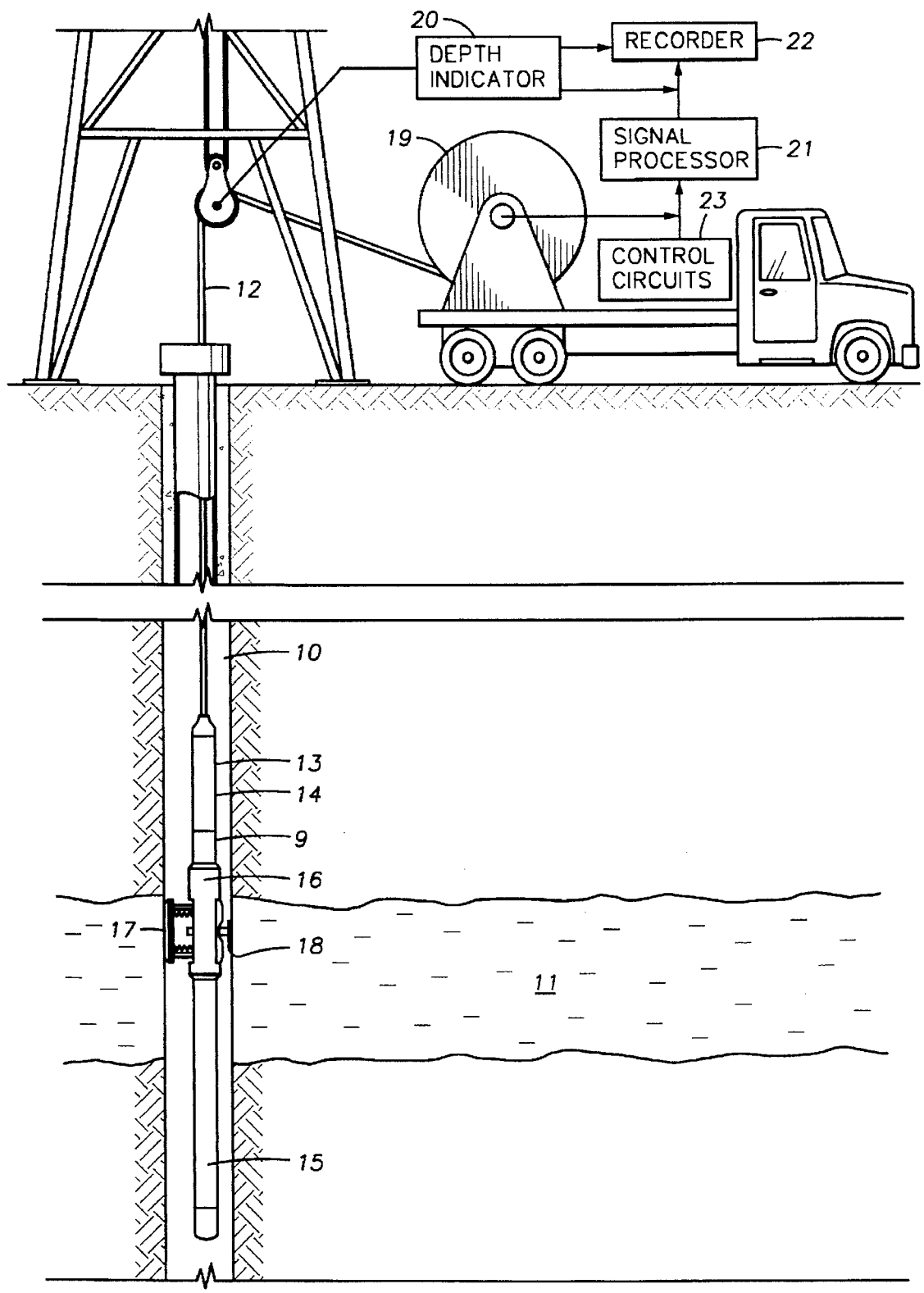
FIG. 1 shows a formation test tool according to the present invention disposed within a wellbore.

A wireline formation test tool is generally shown in FIG. 1 at 13. The tool 13 is attached to one end of an armored electrical cable 12 and is lowered into a wellbore 10 drilled through the earth. The cable 12 can be extended into the wellbore 10 by means of a winch 19 located at the earth's surface.

The tool 13 comprises a back-up shoe and a mechanism for extending the shoe, shown generally at 17, which are disposed within a housing 16. The housing 16 also contains a tubular probe 18 which can be selectively extended and put into contact with the wall of the wellbore 10, as will be further explained. A sample tank 15 can be attached to the lower end of the housing 16 and can be selectively hydraulically connected to the probe 18 in order to store samples of fluids withdrawn from the earth. The probe 18, the back-up shoe 17 and selective valves (not shown) disposed within the housing 16 for operating the probe 18 and the shoe 17 can be of types familiar to those skilled in the art, and can receive hydraulic operating power from an hydraulic power unit 9 attached to the upper end of the housing 16.

The various operating functions of the tool 13, including extension of the shoe 17 and extension of the probe 18, can be controlled by the system operator entering command signals into control circuits 23 which are located at the earth's surface and are electrically connected to the cable 12, as is understood by those skilled in the art. The command signals can be decoded in an electronics unit 14 disposed within the housing 16. As will be further explained, the tool 13 comprises sensors (not shown) for measuring pressure and volume within hydraulic lines (not shown in FIG. 1) connected to a sample chamber (not shown in FIG. 1). Measurements made by the sensors (not shown) are transmitted to the earth's surface as electrical signals generated by the electronics unit 14. At the earth's surface the signals are decoded by a signal processor 21 which is also electrically connected to the cable 12. The decoded signals are reformatted into measurements which can be observed by the system operator and can be recorded by a recorder 22 connected to the signal processor 21.

As the tool 13 is lowered into the wellbore 10, the depth at which the tool is located is indicated by a depth indicator 20 which is in contact with the cable 12 and measures the amount of cable 12 extended into the wellbore 10. When the tool 13 is determined to be positioned adjacent to a formation of interest, shown generally at 11, the system operator enters commands into the control circuits 23 to lock the tool 13 in position by extending the back-up shoe 17. The probe 18 is then extended, and withdrawal of a fluid sample can be initiated.

Figure 2:
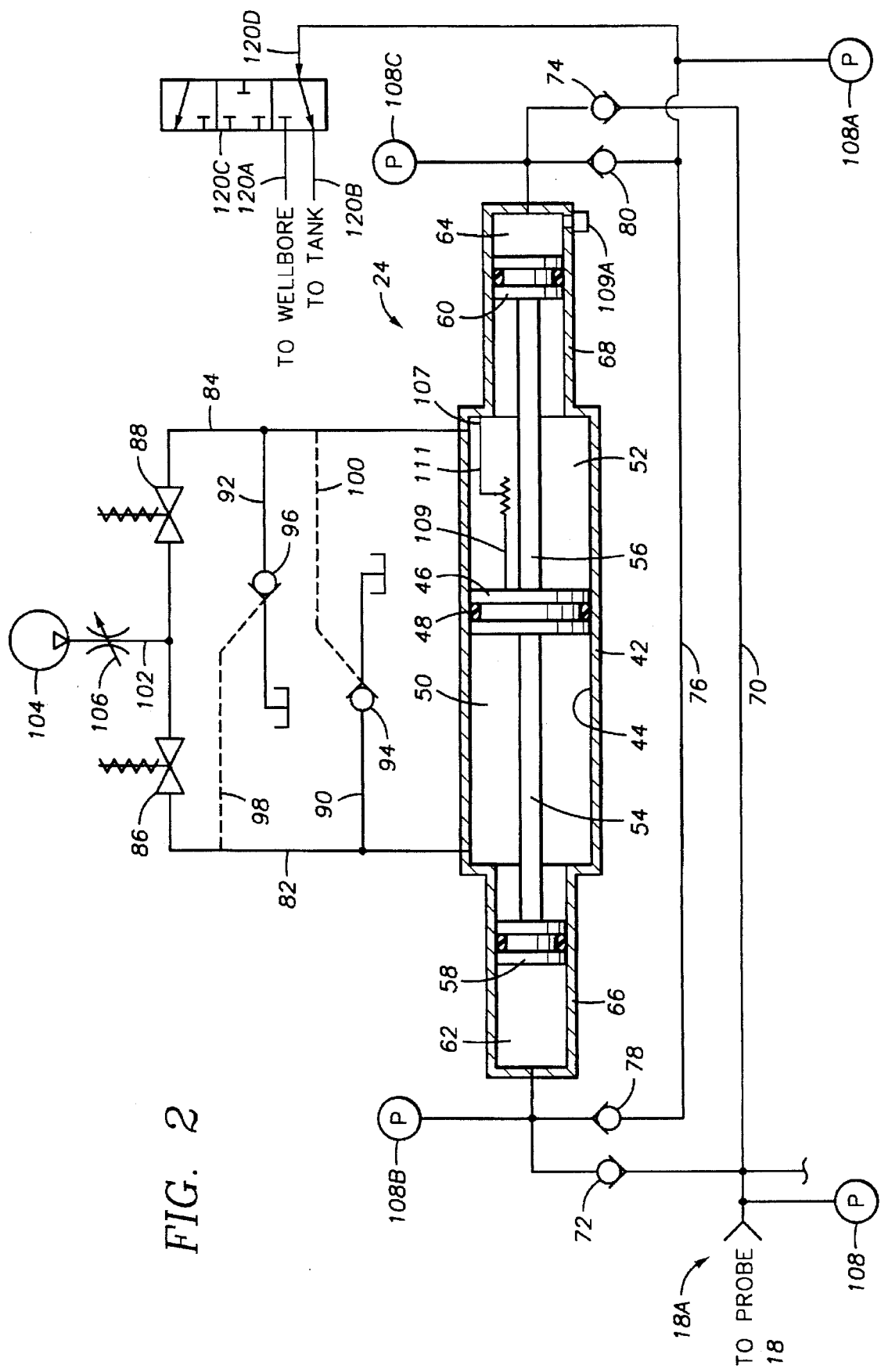
FIG. 2 shows a sampling pump according to the present invention which has a precise measuring apparatus for the pumping chambers.

The means by which a fluid sample can be withdrawn from the formation of interest (11 in FIG. 1) can be better understood by referring to FIG. 2. A bi-directional, hydraulically powered pump, shown generally at 24, can controllably withdraw fluids through the probe (shown as 18 in FIG. 1). If so desired by the system operator, the pump 24 can further be used to discharge the fluids either into the sample tank (shown as 15 in FIG. 1) or into the wellbore (shown in FIG. 1 as 10).

The pump 24 comprises a drive cylinder 44, inside which is located a drive piston 46. The drive piston 46 is sealed against the inner wall of the drive cylinder 44 by an O-ring 48 or similar sealing device. The drive piston 46 is connected on one side to a first drive link 54, and on the other side is connected to a second drive link 56. The first drive link 54 is connected to one side of a first pumping piston 58. The second drive link 56 is similarly connected to a second pumping piston 60 disposed on the opposite side of the drive piston 46 to the first pumping piston 58. The first 58 and the second 60 pumping pistons are each respectively positioned within first 66 and second 68 pump cylinders disposed on opposite ends of the drive cylinder 44. Axial motion of the drive piston 46 is translated into equivalent axial motion of both the first 58 and second 60 pumping pistons, the significance of which will be further explained.

The drive piston 46 is moved axially by selective application of hydraulic pressure to either one side or to the other side of the drive piston 46. Hydraulic pressure is provided by an hydraulic pump 104 which is disposed in the hydraulic power unit (shown in FIG. 1 as 9). The hydraulic pump 104 is connected to a controllable pressure regulator 106 which provides the hydraulic pressure to move the drive piston 46. The discharge pressure from the regulator 106 can be controlled by the system operator entering appropriate commands into the control circuits (shown in FIG. 1 as 23). The controllable regulator discharge provides the system operator with a substantial degree of control over the rate at which the drive piston 46 moves since, as will be further explained, the drive piston 46 must overcome forces of fluid pressures acting on the pumping pistons 58, 60 in order to move.

The discharge from the regulator 106 is provided to hydraulic lines 102. The lines 102 connect to a first 86 and to a second 88 selective hydraulic valve. The selective valves 86, 88 can be operated by control signals sent from the control circuits (shown as 23 in FIG. 1) and decoded in the electronics unit (shown at 14 in FIG. 1). The control signals provide operation of the valves 86, 88 in accordance with the pump 24 function selected by the system operator by entering appropriate commands into the control circuits 23, as will be further explained.

When the first valve 86 is opened, hydraulic pressure is applied through a first hydraulic control line 82 to a first chamber 50 in the drive cylinder 44, which is bounded at one end by the drive piston 46 and at the other end by the first pumping piston 58. The diameters of the first pump cylinder 66, and therefore, the first pumping piston 58 (and consequently their cross-sectional areas) are smaller than the diameter (and cross-sectional area) of the drive piston 46. Hydraulic pressure within the first drive chamber 50 therefore exerts more force on the drive piston 46 than on the first pumping piston 58, which causes motion of the drive piston 46, and all the previously described components that are attached to it, in the direction of the second pump cylinder 68. Hydraulic oil (not shown) is also present in a second drive chamber 52 disposed on the opposite side of the drive piston 46 and axially bounded by the drive piston 46 on one end and the second pumping piston 60 on the other end. As the drive piston 46 moves toward the second pump cylinder 68, the hydraulic oil in the second drive chamber 52 is displaced through a second hydraulic line 84 into a second discharge line 92 connected to a hydraulic oil supply tank (not shown) through a pilot operated check valve 96. The check valve 96 is held open by the operating hydraulic pressure from the line 102 applied through a control line 98 connected to the first hydraulic line 82. A similar, oppositely connected check valve, shown at 94, is connected through a control line 100 to the second hydraulic line 84, and as will be explained, vents the first hydraulic line 82 to the supply tank (not shown) when the drive piston 46 is moved in the opposite direction.

Motion of the drive piston 46 can be reversed by closing the first valve 86 and opening the second valve 88, thereby applying hydraulic pressure through the second hydraulic line 84 to the second drive chamber 52. The operation of the two valves 86, 88 can be performed automatically if the system operator instructs the control circuits 23 to operate the pump 24 continuously. The second pumping piston 60 can be substantially the same diameter as the first pumping piston 58, and thereby be smaller in diameter than the drive piston 46. Therefore hydraulic pressure applied to the second drive chamber 52 will cause motion of the drive piston 46 towards the first pump cylinder 66. As previously explained, the pressure on the second line 84 is also conducted through the control line 100 to open the pilot operated check valve at 94, which enables venting of the first drive chamber 50 to the supply tank (not shown).

Axial motion of the drive piston 46, which as previously explained is translated into equivalent axial motion of the first 58 and second 60 pumping pistons, results in corresponding changes in volume of a first 62 and of a second 64 pump chamber. The pump chambers 62, 64 can be selectively hydraulically connected to the probe 18 in order to withdraw fluid from the formation, as will be further explained.

A particular feature of the present invention which enables direct determination of the volume of the first 62 and the second 64 pump chambers is a displacement sensor, which in the present embodiment can be a linear potentiometer 111 disposed inside the drive cylinder 44 and connected by a link 109 to the drive piston 46. Axial motion of the drive piston 46 results in directly corresponding change in the resistance of the potentiometer 111 as applied to a signal line 107. The resistance as applied to the signal line 107 is converted into a corresponding signal in the electronics unit (shown in FIG. 1 as 14), which signal can be decoded in the signal processor (shown as 21 in FIG. 1) and converted into a measurement of the position of the drive piston 46, and thereby the exact volume of either pump chamber 62, 64, since the axial motion of all three pistons 46, 58, 60 is equivalent. It is contemplated that other means for measuring the axial position (and thereby the volume of the pumping chambers 62, 64) of the drive piston 46 or of the first 58 or second 60 piston can be employed, for example an acoustic travel time sensor disposed within either drive chamber 50 or 52. The linear potentiometer 111 of the present invention is used only as a matter of convenience and should not be construed as an explicit limitation on the means for determining the volume of the pumping chambers 62, 64.

Temperature within the second pumping chamber 64 can be measured by a temperature sensor 109A. The temperature sensor 109A can be of a type known in the art which is operable at very high pressures. Alternatively, the temperature sensor 109A can be connected to a fluid line which connects check valves (shown at 80 and 74) to the second pumping chamber 64. The check valves will be further explained. It is to be understood that the temperature sensor 109A can also be connected to the first pumping chamber 62. The selection of the pumping chamber to which to connect the temperature sensor 109A is only a matter of convenience for the system designer. As is understood by those skilled in the art, the temperature sensor 109A can be of a type which generates an electrical signal corresponding to the temperature to which the sensor 109A is exposed. The electrical signal from the sensor 109A can be conducted to the electronics unit 14 for transmission to the recorder 22. The use of the measurements made by the temperature sensor 109A will be further explained.

Another advantageous feature of the present invention is that the rate of movement of the drive piston 46 can be controlled by the system operator. As previously explained, the drive piston 46 must exert force sufficient to overcome opposing force caused by the formation (shown as 11 in FIG. 1) fluid pressure in the pumping chambers 62, 64 acting on their respective pumping pistons 58, 60 in order to move. The amount of hydraulic pressure applied to the drive piston 46 is controllable by the system operator through the regulator 106. It is therefore possible to operate the drive piston 46 at an hydraulic pressure which just overcomes the formation fluid pressures acting on the pumping pistons 58, 60, in which case the drive piston 46 will move extremely slowly. Moving the drive piston 46 very slowly reduces the possibility, among others, that subtle changes in a relationship between the volume of the pumping chambers 62, 64 and the fluid pressure will go undetected.

When withdrawal of a sample from the formation (shown at 11 in FIG. 1) is begun, the drive piston 46 is typically positioned so that either the first 58 or the second 60 pumping piston is fully extended into its respective pumping chamber 62 or 64. Withdrawal of a sample is begun by application of hydraulic pressure to the appropriate drive chamber 50 or 52 (adjacent to the completely compressed pump chamber into which its pump piston 58 or 60 is fully extended), whereupon the drive piston 46 moves and correspondingly displaces the pumping pistons 58, 60, thereby increasing the volume of the fully compressed pumping chamber 62 or 64.

The first 62 and second 64 pumping chambers are connected, respectively to a first 72 and a second 74 inlet check valve, both of which enable flow from the probe (shown as 18 in FIG. 1) into an inlet flowline 70 (connected as shown at 18A to the probe 18) on the expansion stroke of the respective pumping chamber 62 or 64. The inlet flowline 70 is further connected to a highly precise pressure transducer 108 (which is itself connected to the electronics unit 14) which enables substantially continuous measurement of the pressure in the flowline 70. The use of the pressure measurement made by the transducer 108 in the present invention will be further explained.

During the discharge stroke on one chamber 62 or 64, corresponding to an expansion stroke in the opposing chamber 64 or 62, discharge from the compressing chamber 62 or 64 is conducted, respectively, through a first 78 and second 80 discharge check valve into a discharge line 76.

The discharge line 76 can be selectively hydraulically connected to the sample tank (shown in FIG. 1 as 15), vented to the wellbore (shown in FIG. 1 as 10), or the discharge line 76 can be hydraulically closed at its end. Selective connection of the discharge line 76 can be performed by a four-way solenoid operated valve as shown at 120. The solenoid can operate in response to commands entered into the control circuits (23 in FIG. 1) by the system operator. Operating the solenoid can cause a common port 120D on the valve 120 to be connected to a first selective port 120A which is vented to the wellbore 10, to a second selective port 120B connected to the sample tank 15, or to a third selective port 120C which is closed.

If the system operator desires, for example, to fill the sample tank 15 with fluid withdrawn through the probe 18, the pump 24 can be operated continuously until the tank 15 is filled by automatic selective operation of the valves 86, 88 and 120. Automatic valve control can be performed by the control circuits (shown in FIG. 1 as 23).

A second pressure transducer shown at 108A can be hydraulically connected to the discharge line 76 at a connection position before the common port 120A on the four way valve 120. The purpose of the second transducer 108A will be further explained.

The means by which fluid samples can be controllably withdrawn from the earth formation of interest (11 in FIG. 1) having been described, the method of the present invention by which fluids can be characterized will be explained.

Figure 3:
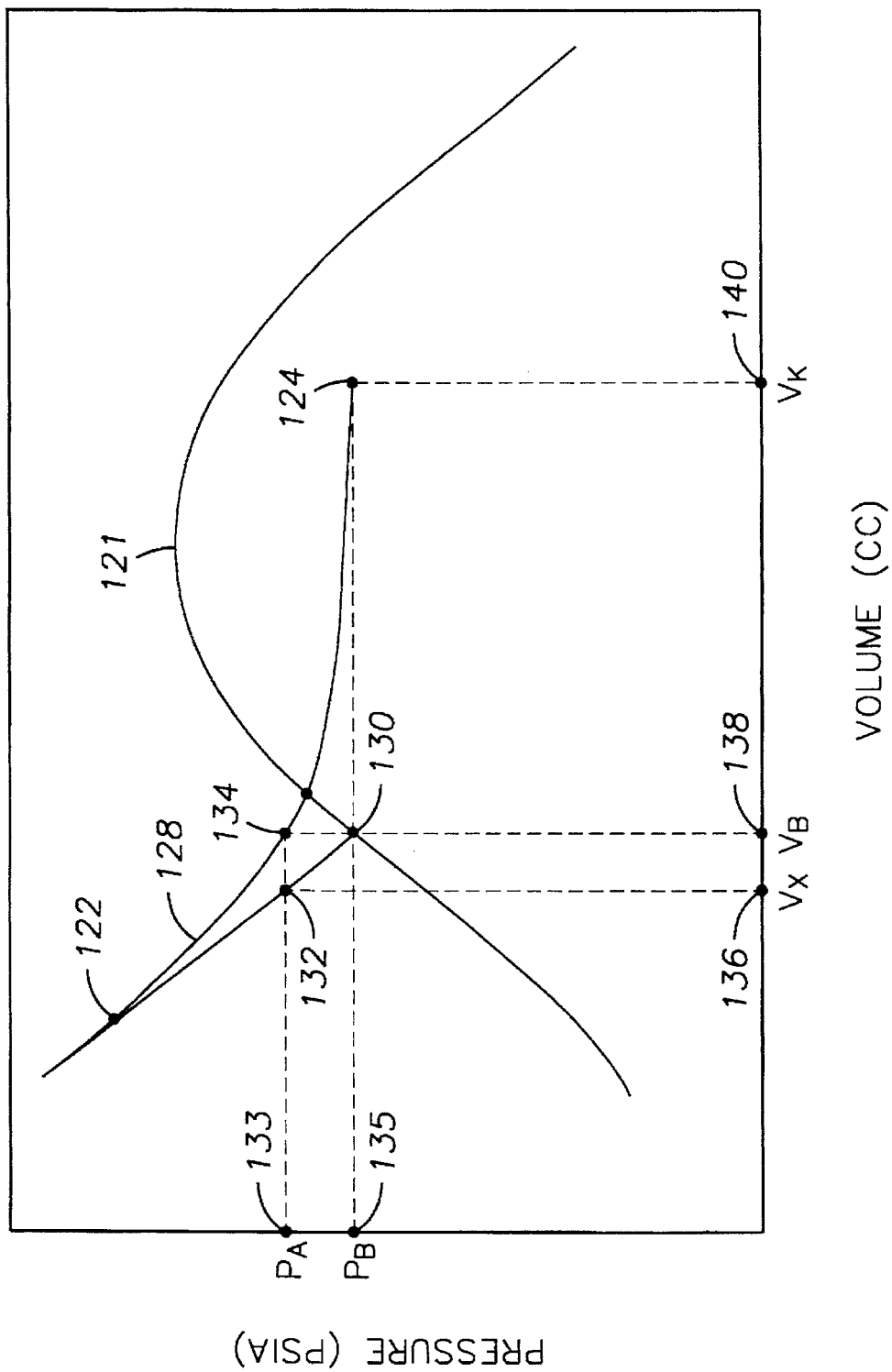
FIG. 3 shows a graphic relationship of pressure with respect to volume for a typical fluid sample from the earth formation.

In a novel aspect of the present invention, the amount of gas dissolved in a fluid sample can be approximately determined. FIG. 3 is a graphic representation of a relationship between pressure and volume of a fluid at a substantially constant temperature. The fluid represented in the graph of FIG. 3 can be a mixture of crude oil (a liquid phase) and natural gas (a gaseous phase). A relationship with respect to the pressure and the volume between the existence of principally gaseous and principally liquid phases of that fluid is described by a curve, shown generally at 121, and known to those skilled in the art as a "bubble point" curve. At pressures generally higher than the bubble point curve 121 for any particular volume of fluid, the natural gas phase of the mixture tends to be substantially dissolved in the liquid phase. At pressures below the bubble point curve 121 at any particular volume, gas can exsolve from the oil and exist as a free gaseous phase in equilibrium with the liquid phase.

As previously described herein, a sample can be withdrawn into the inlet line (shown as 70 in FIG. 2) by the pump (shown in FIG. 2 as 24). Tests can be performed on a part of the fluid sample which is withdrawn through the inlet line 70 and into the one of the pumping chambers (shown as 62 and 64 in FIG. 2) which is on its intake stroke. Testing the sample is initiated by the system operator entering a command into the control circuits (23 in FIG. 1) to operate the four way valve (120 in FIG. 2) so as to hydraulically close the discharge line (76 in FIG. 2). Closing the discharge line 76 traps the sample within a controllable volume. The controllable volume includes the volume of the one pumping chamber (62 or 64) in which the fluid is being drawn, and the discharge line 76 as far as the four-way valve 120.

Testing can continue, as will be explained, by operating the pump 24 in the reverse direction as previously described herein so as to expand the volume of the fluid sample. While the sample is being expanded, the pressure can be observed by the system operator. As previously described herein, the pressure in the discharge line 76 is measured by the second transducer (108A in FIG. 2).

Referring again to FIG. 3, the pressure which is observed by the system operator during expansion of the trapped sample can be represented by a curve, shown generally at 128. Curve 128 exhibits a highly sloping, substantially linear portion ending at a point shown at 122. The linear expansion portion of curve 128 is typically a characteristic of expansion of liquid. The slope of the curve 128 at volumes below that represented at point 122 are characteristic of a property of the liquid known as compressibility. At sample volumes larger than the volume at point 122, the volume is large enough (and the pressure is correspondingly reduced enough) so that gas which may be dissolved in the liquid can begin to exsolve from the liquid. As the volume is further increased, more gas may exsolve from the liquid until substantially all the gas is exsolved, as shown generally at point 124.

A "perfect", or ideal, solution of gas in liquid would not exhibit a pressure decrease upon volumetric expansion in a manner characterized by curve 128. Instead, a "perfect" liquid sample having dissolved gas would continue to expand in a manner corresponding exactly to the liquid compressibility (in effect continuing the linear portion of the expansion curve), until the so-called bubble pressure is reached, the bubble pressure being shown at point 130. Continued expansion of the "perfect" solution would result in all the additional expansion volume being occupied by exsolved gas, so that substantially no change in pressure would occur in the expanding sample chamber. This effect is characterized by a substantially straight-line expansion observable between point 130 and point 124 in FIG. 3.

In contrast, in a sample of "real", or actual fluid withdrawn from the earth formation (11 in FIG. 1), the exsolution of gas during expansion of the sample can occur slowly relative to the amount of time taken to expand the sample. The relatively slow exsolution of gas causes the expansion pressure response as exhibited by curve 128. By straight-line extrapolation of the linear, sloping, liquid-expansion portion of curve 128 located at volumes equal to or less than shown at point 122, and by straight-line extrapolating the exsolved gas-expansion portion occurring at volumes larger than at point 124, back to a point of intersection, the bubble pressure of the fluid sample can thus be determined. As previously explained, the bubble pressure is shown at point 130.

A difference exists between the actual sample pressure and the pressure extrapolated from the bubble-pressure, at the volume corresponding to the bubble pressure. The difference in pressures is indicative of the amount of gas dissolved in the liquid phase of the sample. The actual sample pressure which is measured, at a sample volume corresponding to the extrapolated bubble pressure, is shown at point 134. A volume of liquid, that particular volume being represented by the difference between the actual sample volume at the bubble pressure, shown at point 134, and the volume of a "perfect" sample of liquid at the same pressure, as shown at point 132, can be represented as being expanded so as to exsolve gas having a volume represented by the expansion from the bubble pressure volume, at point 130, and the fully gas-exsolved volume at point 124.

The "perfect" sample volume is represented by the variable $V_x$ and is shown on the volume axis of the graph at point 136. The bubble pressure volume is represented by the variable $V_b$ and is shown on the volume axis of the graph at point 138. Similarly, the fully exsolved sample volume $V_k$ is shown at point 140. The derived sample expansion is characterized by a change in sample pressure shown between points 133 and 135 and represented by variables $P_a$ and $P_b$, respectively. A gas-oil ratio (GOR), known in the art for describing a volume of natural gas which is associated with production of a specific quantity of crude oil, can be determined by the expression:

$$GOR = \frac{(V_k - V_b)}{(V_b - V_x)} \times \frac{(P_a + P_b)}{5.23} \qquad (1)$$

in which the value 5.23 is a constant of proportionality to scale the GOR into units, familiar to those skilled in the art, of cubic feet of gas per stock-tank barrel of oil. As is known to those skilled in the art, the expression "stock tank" barrels of oil represents oil volume after the oil has been brought to the pressure and temperature conditions at the earth's surface.

After the bubble pressure, shown at 130, is determined it is possible to determine whether the sample includes a system of liquid and dissolved gas consisting essentially of hydrocarbons by using a method called the "Y-correlation". The Y-correlation is described, for example, in "Volumetric and Phase Behavior of Oilfield Hydrocarbon Systems", M. B. Standing, Society of Petroleum Engineers of AIME, Dallas, 1977. The Y-correlation can be determined according to the following expression:

$$Y = \frac{\frac{P_b}{P} - 1}{\frac{V}{V_b} - 1} \quad \text{when } P < P_b \qquad (2)$$

Figure 4:
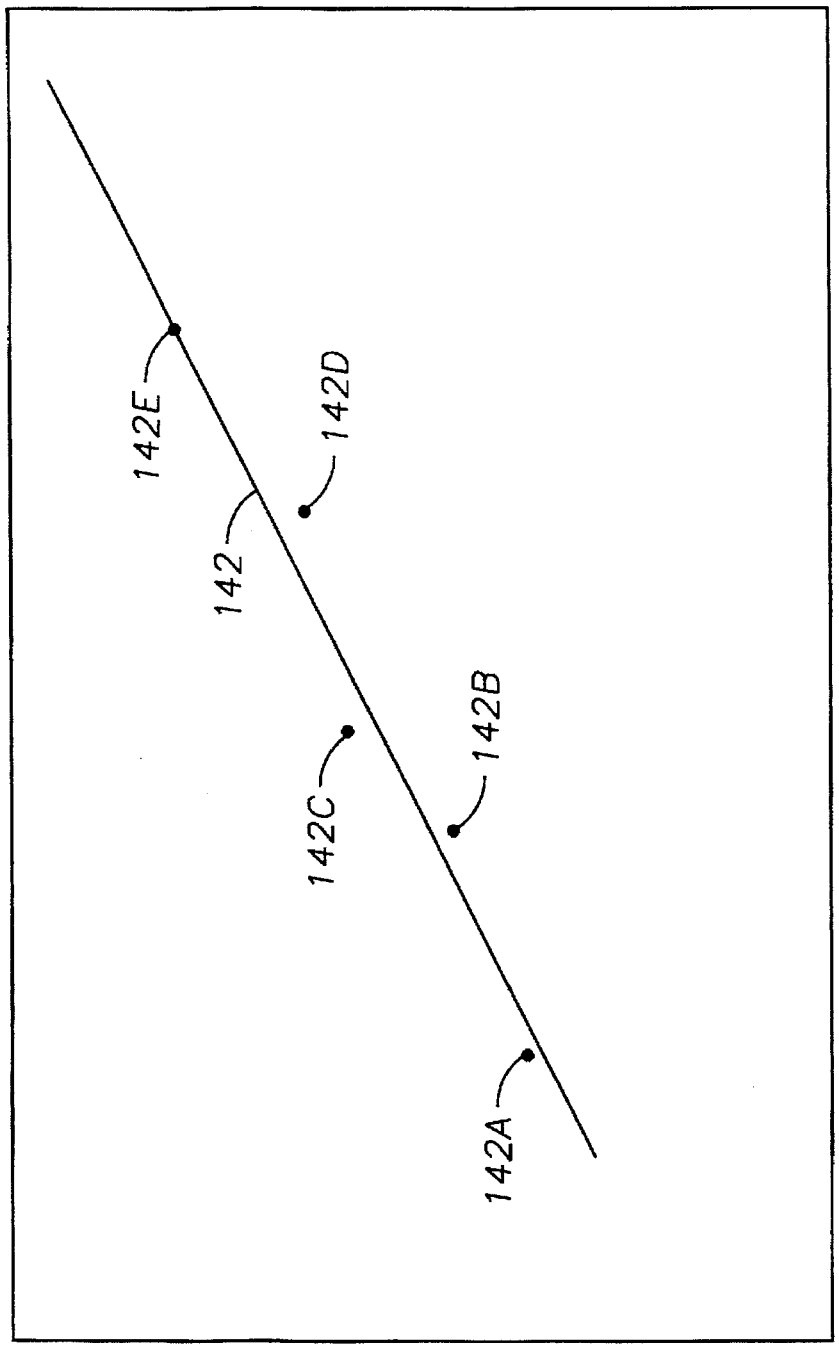
FIG. 4 shows a graphic relationship of a pressure-volume relationship called the Y-correlation used to determine presence of hydrocarbons.

As is understood by those skilled in the art, a graph of calculated Y value with respect to the pressure at which the Y-values are calculated is indicative of whether the dissolved gas in the sample substantially consists of hydrocarbons. An example of a graph of Y with respect to pressure is shown for example in FIG. 4. The graph in FIG. 4 shows values of Y at their respective pressures, as points 142A through 142E. A best fit curve drawn through the points, shown at 142 in the example of FIG. 4, is a straight line. As is understood by those skilled in the art, straight-line correspondence of Y with respect to pressure indicates that the system of dissolved gas and liquid in the sample can consist primarily of hydrocarbons.

DESCRIPTION OF ALTERNATIVE EMBODIMENTS

In another embodiment of the invention it is possible to estimate the gas-oil ratio (GOR) and the compressibility of the fluid while it is being withdrawn by the pump (24 in FIG. 2). By making an estimate of fluid compressibility and gas-oil ratio while withdrawal of the sample is in progress, the system operator may be able to determine when the fluid being withdrawn through the probe (18 in FIG. 1) consists substantially of native fluid from the formation (11 in FIG. 1) rather than mud filtrate. Mud filtrate may be forced into the formation 11 from within the wellbore (10 in FIG. 1) by differential pressure, as is understood by those skilled in the art. Determination of when the fluid being withdrawn consists of native fluid can assist the system operator in minimizing the amount of time needed to withdraw a sample from the formation (11 in FIG. 1).

Figure 5:
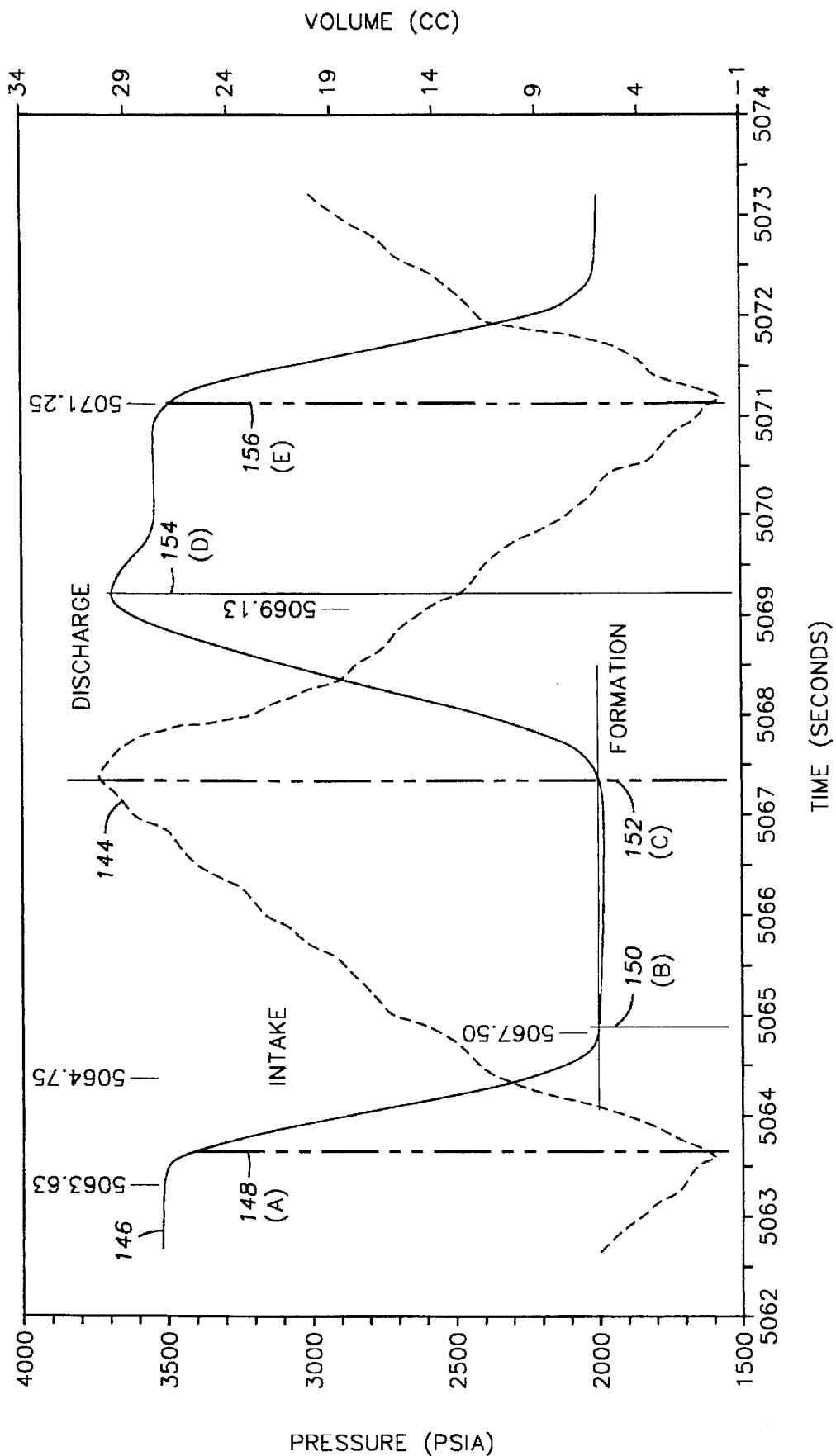
FIG. 5 shows a graph of pressure and volume, with respect to time, of the sample chamber of the tool of the present invention.

Referring now to FIG. 5, which is a graphic representation of sample pressure and sample volume with respect to time, a method by which the compressibility and gas-oil ratio of the fluid being moved by the pump (24 in FIG. 2) will be explained. One curve, shown as 146 in the graph of FIG. 5, is a representation of the pressure within either one of the two pumping chambers (shown for example in FIG. 2 as 64 and 62) during a pumping cycle. A pumping cycle includes an intake stroke, in which the chamber (62 or 64) volume is expanded from its minimum to its maximum, and a discharge stroke in which the reverse volume change occurs. Pressure within each chamber 62, 64 can be measured by additional pressure transducers, shown for example in FIG. 2 at 108B and 108C, respectively. Signals from the additional transducers 108B, 108C can be sent to the electronics unit (14 in FIG. 1) for transmission to the signal processor (21 in FIG. 1) and recorder (22 in FIG. 1) whereupon the pressure measurements can be observed and recorded. Chamber volume in both pumping chambers 62, 64 can be continuously determined, as previously explained, by the linear potentiometer apparatus (107 in FIG. 2), so that a record of volume can be generated. A second curve shown at 144 corresponds to the volume of the pumping chamber (62 or 64). It is to be understood that the method described herein is applicable to either chamber 62 or 64. Selection of the second pumping chamber 64 as described herein is only a matter of convenience for clarity of the description. As the intake stroke begins, shown on the volume curve 144 at a time shown at A and further indicated by reference numeral 148, the chamber 64 volume begins to increase and the pressure within the chamber 64 begins to decrease. In order for fluid flow into the chamber 64 to begin however, the pressure within the chamber 64 must decrease to below the pressure present in the intake line (70 in FIG. 2), which typically is equal to the fluid pressure in the formation (11 in FIG. 1) as shown B and further indicated by reference numeral 150. Therefore, some of the increase in chamber 64 volume of the intake stroke is consumed by expansion of the fluid in the chamber 64 so its pressure drops below the intake line 70 pressure. As the chamber 64 is expanded further, the fluid starts to flow into the chamber 64. At the end of the intake stroke, shown C and indicated by reference numeral 152, some fluid can continue to flow into the chamber 64 because of inertia, which can slightly elevate the pressure. At the end of the intake stroke the chamber 64 volume immediately begins to decrease, since the end of the intake stroke coincides with commencement of the discharge stroke. Fluid flow out of the chamber 64 cannot begin, however, until the fluid pressure in the chamber 64 at least slightly exceeds the pressure in the discharge line (76 in FIG. 2). Initiation of fluid flow into the discharge line 76 is indicated at D (and is indicated by reference numeral 154). Fluid is then displaced from the chamber 64 until the chamber 64 is compressed to its smallest volume, as indicated at E and further designated by reference numeral 156. At this point one pumping cycle is completed.

As previously explained, the fluid discharged from the pump 24 during the discharge stroke can be selectively directed to the sample tank (15 in FIG. 1) or can vented to the wellbore (10 in FIG. 1) by the system operator selectively operating the four way valve (120 in FIG. 2) to the corresponding position.

As is understood by those skilled in the art, the efficiency (η) of the pump (24 in FIG. 2) can be described as the volume of fluid actually displaced by the pump 24, with respect to the amount of change in chamber volume of the pump 24 (also referred to herein as the "stroke volume" or $V_{stroke}$). For the pump as represented by the graph in FIG. 5, efficiency on the intake stroke is represented by:

$$\eta_{intake} = \frac{V_C - V_B}{V_C - V_A} \quad (3)$$

and similarly for the efficiency on the exhaust stroke:

$$\eta_{discharge} = \frac{V_E - V_D}{V_E - V_C} \quad (4)$$

where the subscripted "V" terms in the previous efficiency equations refer to the corresponding pumping chamber volumes at points A through E, respectively.

The fluid compressibility (β) can be determined by the expression:

$$\beta = \left(1 - \frac{\eta_{discharge}}{\eta_{intake}}\right) \times \frac{1}{(P_{discharge} - P_{intake})} \quad (5)$$

Fluid compressibility can be determined while pumping is in progress, for example, by programming the recorder (22 in FIG. 1) to perform calculations according to the previous expressions for pump efficiency and compressibility. The system operator can then observe the calculated fluid compressibility while pumping is in progress. Changes in fluid compressibility thus calculated which are observed during pumping may correspond to changes in the composition of the fluid being pumped, particularly if the fluid being pumped ceases to consist of the previously described mud filtrate and instead consists of the native fluid from the formation (11 in FIG. 1).

It is further possible to estimate the previously described gas-oil ratio of the fluid being pumped, while pumping is in progress, by an addition to the present embodiment of the invention. If the system operator has selectively operated the four way valve (120 in FIG. 2) to direct the discharge from the pump (24 in FIG. 2) into the sample tank (15 in FIG. 1), then knowledge of the volume of the sample tank 15 can be used in estimating the gas-oil ratio of the fluid discharged into the sample tank 15. In this description of the addition to the present embodiment of the invention, the variables which are designated by the description "intake" correspond to fluid withdrawn from the formation (11 in FIG. 1), and the variables designated "discharge" correspond to the fluid discharged into the sample tank 15. If the fluid from the formation 11 consists of a mixture of liquid and gas, then the following relationship describes the volume of "intake" fluid:

$$V_{intake} = V_{gas(intake)} + V_{liquid(intake)} \quad (6)$$

and the volume discharged into the sample tank 15, which volume is known, is:

$$V_{discharge} = V_{gas(discharge)} + V_{liquid(discharge)} \quad (7)$$

The intake gas volume can be determined by the following expression:

$$V_{gas(intake)} = \quad (8)$$

$$\frac{V_{stroke} \times \eta_{intake}(1 - \beta_{liquid}(P_{discharge} - P_{intake})) - V_{discharge}}{\left(1 - \frac{P_{intake}}{P_{discharge}} - \beta_{liquid} \times (P_{discharge} - P_{intake})\right)}$$

Finally, the gas-oil ratio (GOR) can be estimated by the expression:

$$GOR = \frac{V_{gas(intake)}}{(V_{stroke} \times \eta_{intake}) - V_{gas(intake)}} \quad (9)$$

In another embodiment of the invention, it is possible to estimate the viscosity of the fluid being withdrawn by the pump (24 in FIG. 2). As previously described herein, and as can be observed by again referring to FIG. 2, the pressure at the intake line 70 and at the discharge line 76 can be measured by pressure transducers 108 and 108A respectively connected thereto. As fluid is displaced through the lines 70 and 76, a differential pressure can be developed which is related to the viscosity of the fluid being pumped. The differential pressure can correspond to viscosity because the pump 24, as previously explained, has two opposing chambers 62, 64 and fluid can be simultaneously drawn by one chamber 62 and discharged by the other chamber 64. Flow in the lines 70, 76 can therefore be substantially continuous during pumping. The differential pressure ΔP developed between the intake 70 and discharge 76 lines can be related to the fluid viscosity μ by following expression:

$$\mu = \frac{\Delta P}{\overline{V}} \times K_v \quad (10)$$

where $K_v$ is a proportionality constant for each tool which can be determined in a calibration using fluid having a known viscosity displaced by the pump 24, and the overbar - V term is the average velocity of the fluid through the lines. The average velocity is related to the volume of fluid being pumped, which can be determined as previously explained herein, and the apparent cross-sectional area of the lines 70, 76, which is known.

By determining the fluid viscosity, it can be possible to determine whether the fluid being drawn by the pump 24 is mud filtrate or native fluid. Native fluid can be further characterized as to it composition by knowledge of its viscosity, as is understood by those skilled in the art.

Figure 6:
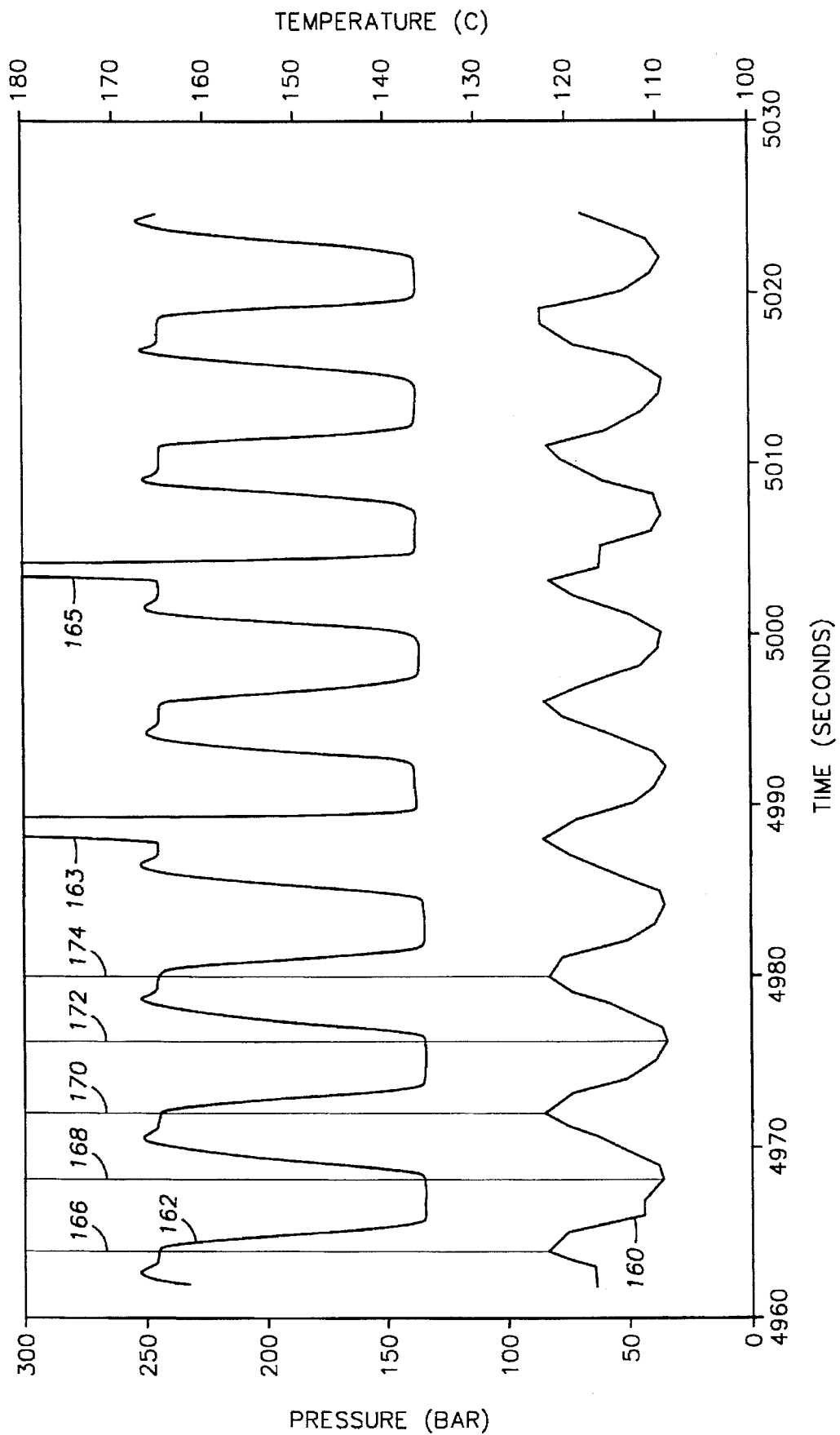
FIG. 6 shows a graph of pressure and temperature of a fluid being as it is being pumped.

In another novel aspect of the present invention it is possible to determine whether the fluid within the pumping chamber (such as 64 in FIG. 2) consists mainly of gas or a liquid by observation of the temperature of the fluid during pumping. As previously described, a temperature sensor (shown in FIG. 2 as 109A) is in hydraulic communication with the second pumping chamber 64. As fluid is moved by the pump (24 in FIG. 2), changes in temperature of the fluid can be observed. The observed changes in temperature can correspond to the phase composition of the fluid being pumped. FIG. 6 shows a graph of pressure, shown as curve 162 and temperature, shown as curve 160, of fluid in the second pumping chamber (64 in FIG. 2) while pumping is in progress. The curves 160, 162 in FIG. 6 are from an actual test of an testing tool according to the present invention. Spikes in the pressure curve 162, which can be observed at 163 and 165 therefore do not correspond to real changes in pressure but are attributable to errors in data telemetry between the electronics unit (14 in FIG. 1) and the signal processor (21 in FIG. 1). As shown in FIG. 6, peaks in temperature correspond to the end of the discharge strokes of the pump (24 in FIG. 2), as can be observed at 166, 170 and 174, and periodic minima in the temperature, as can be observed at 168 and 172, correspond to the end of intake strokes of the pump 24. The amount of difference in temperature between the peaks and periodic minima corresponds to the phase composition of the fluid being pumped. The temperature curve 160 which exhibits peak-to-peak temperature variations of about 10 degrees Celsius, in FIG. 6 is indicative of gas. Liquids typically exhibit differences in temperature while pumping of approximately one to two degrees Celsius, depending on liquid compressibility. Observation of the difference in temperature can provide information which can confirm other determinations of compressibility and fluid composition made according to the present invention.

Other embodiments providing the improvement over the prior art as described in the present invention will be readily devised by those skilled in the art. The description of the invention provided herein is to be used only as an example and not as a limitation on the scope of the invention. The scope of the invention should only be limited only by the claims appended hereto.

What is claimed is:

1. A method of determining an amount of dissolved gas in a fluid sample, comprising the steps of:

hydraulically confining said fluid sample;

expanding said fluid sample while measuring pressure and volume of said fluid sample;

determining a first volume and a first pressure at which a rate of change in said pressure with respect to said volume deviates from a linear relationship;

determining a second volume and a second pressure at which additional expansion of said fluid sample causes substantially no change in said pressure of said fluid sample;

extrapolating said first pressure and said first volume by said linear relationship so as to intersect an extrapolation of said second volume and said second pressure, said extrapolation of said second volume and said second pressure having substantially no change in pressure with respect to volume, thereby determining a bubble point, said bubble point including a bubble point pressure and a bubble point volume;

determining a third pressure, said third pressure including said pressure of said fluid sample measured at said bubble point volume;

determining an extrapolated sample volume at said third pressure by extrapolating said linear relationship from said bubble point to a sample volume of said linear relationship corresponding to said third pressure; and determining a volume of gas dissolved in said fluid sample by linearly scaling a difference between said bubble point volume and said extrapolated sample volume with respect to a difference between said second volume and said bubble point volume.

2. The method as defined in claim 1 further comprising the steps of:

measuring temperature of said fluid sample proximal to a pumping chamber of a pump used to withdraw said fluid sample, said step of measuring performed while said pump is operating;

determining a difference in said temperature between an intake stroke of said pump and a discharge stroke of said pump; and determining whether said fluid sample comprises gas by comparing said difference in said temperature to differences in temperature corresponding to the presence of gas.

3. The method as defined in claim 1 wherein said fluid sample is withdrawn from an earth formation by an electric wireline formation testing tool comprising a sample chamber having a means for measuring volume of said sample chamber and means for measuring pressure of said fluid sample in said sample chamber.

4. The method as defined in claim 1 further comprising the step of characterizing a composition of said fluid sample by determining a Y-correlation.

5. The method as defined in claim 4 wherein said fluid sample is determined to comprise a system of gas dissolved in liquid, said gas and said liquid comprising hydrocarbons when said Y-correlation forms a substantially linear relationship with respect to pressure of said fluid sample.

6. A method of determining when a fluid being withdrawn from an earth formation by a pump in a formation testing tool includes gas therein, comprising the steps of:

measuring temperature of said fluid proximal to a pumping chamber of said pump while said pump is operating;

determining a difference in said temperature between an intake stroke of said pump and a discharge stroke of said pump; and determining whether said gas is present in said fluid by comparing said difference in said temperature to differences corresponding to the presence of gas.

* * * * *